United States Patent [19]

Fujita et al.

[11] Patent Number: 5,552,453
[45] Date of Patent: Sep. 3, 1996

[54] WATER-ABSORPTIVE MATERIAL AND METHOD OF PRODUCING WATER-ABSORPTIVE MOLDED PRODUCT

[75] Inventors: Takeshi Fujita, Uji; Katsuaki Matsuo, Kyoto; Osamu Kakishita, Nagahama, all of Japan

[73] Assignees: Mitsubishi Plastics, Inc., Tokyo; Dai-Ichi Kogyo Seiyaku Co., Ltd., Kyoto, both of Japan

[21] Appl. No.: 357,756

[22] Filed: Dec. 16, 1994

[51] Int. Cl.$^6$ ............................................. C08J 3/28
[52] U.S. Cl. .......................................... 522/165; 428/411.1
[58] Field of Search ........................ 522/165; 428/411.1

[56] References Cited

U.S. PATENT DOCUMENTS

| | | | |
|---|---|---|---|
| 5,059,630 | 10/1991 | Fujita et al. | 521/61 |
| 5,248,431 | 9/1993 | Fujita et al. | 252/49.3 |

FOREIGN PATENT DOCUMENTS 5-339384  12/1993  Japan .

OTHER PUBLICATIONS

English Abstracts of JP 5–339384.

*Primary Examiner*—Mark Chapman
*Attorney, Agent, or Firm*—Oblon, Spivak, McClelland, Maier & Neustadt

[57] ABSTRACT

An object of the present invention is to provide a water-absorptive material having a satisfactory water-absorptivity in an ion-exchanged water as well as an ionic aqueous solution and also having a satisfactory thermoplastic moldability, and also to provide a water-absorptive molded product having an excellent fabricability including heat-sealability.

Thus, the present invention provides a water-absorptive material crosslinked by irradiation with an ionizing radiation or ultraviolet rays, which comprises a hydrophilic high molecular compound having a weight average molecular weight of at least 10,000 obtained by reaction of (i) a polyalkylene oxide compound having an organic compound containing two active hydrogen groups addition-polymerized with an alkylene oxide comprising ethylene oxide as the main component and (ii) a polycarboxylic acid, a polycarboxylic acid anhydride, a lower alkyl ester of polycarboxylic acid or a diisocyanate.

4 Claims, No Drawings

WATER-ABSORPTIVE MATERIAL AND METHOD OF PRODUCING WATER-ABSORPTIVE MOLDED PRODUCT

BACKGROUND OF THE INVENTION

1. Field of the Invention

The present invention relates to a novel water-absorptive material and a method of producing a water-absorptive molded product.

2. Discussion of Background

Heretofore, a highly water-absorptive polymer has been widely used for sanitary goods such as a diaper and a sanitary towel, agricultural and gardening goods such as a water-holding agent, and other various uses which require water-absorptivity, and its utility is generally appreciated. Generally known examples of the water-absorptive polymer include polyacrylate type, starch type or cellulose type polymers in various forms of powder or fiber.

These known polymers exhibit a satisfactory water-absorptivity to ion-exchanged water (deionized water), but do not exhibit a satisfactory water-absorptivity to an ionic aqueous solution. However, most of these water-absorptive polymers are used in connection with an ionic aqueous solution, and it is therefore strongly demanded in this technical field to improve the water-absorptivity of these polymers in the ionic aqueous solution.

These water-absorptive polymers alone can not be molded into a sheet or the like, and they are used in a form of powder. Thus, it is necessary to disperse and maintain the powdery polymer in a fibrous substrate such as a paper or a non-woven cloth, and it is therefore inconvenient to prepare a final product. Also, the final product thus prepared sometimes do not have a high water-absorptivity. Moreover, these conventionally known water-absorptive polymers are usually poor in fabricability, and it is therefore hard to be stretched or made into a composite.

There are some water-absorptive polymers which can be molded into products by themselves, but their types are limited. Thus, there are few water-absorptive polymers which satisfy both fabricability and high water-absorptivity.

SUMMARY OF THE INVENTION

An object of the present invention is to provide a water-absorptive material having a satisfactory water-absorptivity in an ion-exchanged water as well as an ionic aqueous solution and also having a satisfactory thermoplastic moldability, and also to provide a water-absorptive molded product having an excellent fabricability.

Thus, the present invention provides a water-absorptive material crosslinked by irradiation with an ionizing radiation or ultraviolet rays, which comprises a hydrophilic high molecular compound having a weight average molecular weight of at least 10,000 obtained by reaction of (i) a polyalkylene oxide compound having an organic compound containing two active hydrogen groups addition-polymerized with an alkylene oxide comprising ethylene oxide as the main component and (ii) a polycarboxylic acid, a polycarboxylic acid anhydride, a lower alkyl ester of polycarboxylic acid or a diisocyanate.

The present invention further provides a method for producing a water-absorptive molded product, which comprises (a) molding a hydrophilic high molecular compound obtained by reaction of (i) a polyalkylene oxide compound having an organic compound containing two active hydrogen groups addition-polymerized with an alkylene oxide comprising ethylene oxide as the main component and (ii) a polycarboxylic acid, a polycarboxylic acid anhydride, a lower alkyl ester of polycarboxylic acid or a diisocyanate, and (b) crosslinking the molded product by irradiation with an ionizing radiation or ultraviolet rays.

DETAILED DESCRIPTION OF THE INVENTION

The present invention is further described in more details hereinafter.

A hydrophilic high molecular compound used in the present invention is obtained by reacting a polyalkylene oxide compound with a polycarboxylic acid or the like, and the polyalkylene oxide compound is prepared by addition-polymerizing an organic compound containing two active hydrogen groups with an alkylene oxide comprising ethylene oxide as the main component.

Examples of the organic compound containing two active hydrogen groups include ethylene glycol, propylene glycol, polyethylene glycol, polypropylene glycol, polytetramethylene glycol, 1,6-hexanediol, aniline, bisphenol A and the like.

Examples of an alkylene oxide comprising ethylene oxide as the main component include ethylene oxide alone or a mixture of ethylene oxide (the main component) with propylene oxide, butylene oxide, styrene oxide, an $\alpha$-olefin epoxide or glycidyl ethers, or the like.

The addition-polymerization of an alkylene oxide and an organic compound containing two active hydrogen groups may be conducted by a known method, but addition reaction of ethylene oxide with other alkylene oxides may be optionally conducted by mixing or block-polymerizing. The polyalkylene oxide compounds thus prepared should preferably have a weight average molecular weight of at least 100.

Examples of a polycarboxylic acid to be reacted with the polyalkylene oxide compound include carboxylic acids such as phthalic acid, isophthalic acid, terephthalic acid, adipic acid, fumaric acid, malonic acid, maleic acid, sebacic acid, dimer acid, pyromellitic acid and the like. Anhydrides of these carboxylic acids or lower alkyl esters of these carboxylic acids may also be used.

Examples of the lower alkyl esters include ethyl ester, dimethyl ester, diethyl ester and the like. Most preferable examples include dimethylterephthalate, dimethylphthalate, dimethylisophthalate, dimethylsebacate and pyromellitic anhydride.

The polymerization reaction is conducted preferably at a temperature of from 120° to 250° C. under a pressure of from $10^{-4}$–760 Torr.

Also, examples of a diisocyanate to be reacted with the polyalkylene oxide compound include tolylene diisocyanate, diphenylmethane diisocyanate, hexamethylene diisocyanate, isophorone diisocyanate, xylilene diisocyanate, 4,4-methylene-bis-(cyclohexylisocyanate), and the like.

This urethane-forming reaction is conducted, for example, by mixing a polyalkylene oxide with a diisocyanate at a NCO/OH equivalent ratio in the range of 1.5–0.5 and reacting the mixture at 80°–150° C. for 1 to 5 hours.

The hydrophilic high molecular compound thus obtained should preferably have a weight average molecular weight of at least 10,000. If the weight average molecular weight is less than 10,000, the hydrophilic high molecular compound becomes poor in respect of mechanical strength and fabricability.

The hydrophilic high molecular compound may be crosslinked by irradiation with an ionizing radiation or ultraviolet rays in a form of powders or pellets, and may be used as a water-absorptive material as it is, or it may be molded into various forms before being used.

Molding can be conducted by thermoplastic molding. Thus, the high molecular compound is melted, molded into various desired forms such as a film, a sheet, a board, a tubular article, or others, and then cooled. The molding method may be the same as those used for molding polyethylene, polyvinyl chloride or the like. Thus, when it is molded into a film or a sheet, it may be done by extrusion-molding or calender-molding. When other molded products are desired, they can be prepared by injection-molding or press-molding. A molding temperature generally ranges from 80° to 150° C.

The above-mentioned high molecular compound has a stable thermoplastic moldability and exhibits a satisfactory extensible property during extrusion molding as compared with a polymer comprising ethylene oxide only. This is considered to be mainly because its crystallinity is low.

The molded product thus obtained is water-soluble, but becomes water-insoluble when crosslinked by irradiation with an ionizing radiation or ultraviolet rays. Examples of the ionizing radiation include electron radiation, γ-ray, X-ray and the like. An appropriate absorbed dose of the ionizing radiation is from 0.5 to 20 Mrad. If the absorbed dose is less than 0.5 Mrad, the molded product remains water-soluble and does not exhibit water-absorptivity. On the other hand, if the absorbed dose is larger than 20 Mrad, water absorptivity scale factor becomes unfavorably extremely low. The "water absorptivity scale factor" used herein is referred to as a ratio value obtained by dividing the weight of a molded product after sufficiently absorbing water by the weight of a molded product before absorbing water.

Now, the present invention will be described in further detail with reference to Examples. However, it should be understood that the present invention is by no means restricted to such specific Examples.

EXAMPLE 1

2.2 parts by weight of dimethylterephthalate was blended with 100 parts by weight of polyethylene glycol (weight average molecular weight: 10,000) having ethylene glycol addition-polymerized with ethylene oxide, and the resultant blend was subjected to polyesterification reaction to obtain a hydrophilic high molecular compound (hereinafter simply referred to as "Compound") having a weight average molecular weight of 130,000. The compound thus obtained was extruded through a single screw extruder at a T die temperature of 90° C. to obtain a cast sheet having a thickness of 100 μm.

Although the sheet was thin, the extrusion-molding provided a flexible sheet having a smooth and glossy surface without breaking since its melted resin is satisfactorily extensible.

The extrusion-molded sheet was irradiated with electron radiation by an electron radiation irradiating apparatus at an accelerated voltage of 200 kV and at an absorbed dose of 3 Mrad to obtain a water-absorptive sheet. The water absorptivity scale factor of the water-absorptive sheet thus obtained was 30 times in a physiological saline solution (ionic aqueous solution), and substantially the same result was obtained also in distilled water.

The sheet thus obtained had a tensile strength of 300 kg/cm$^2$ at 23° C. and an elongation of 1,100% (JIS K6761). This sheet was biaxially stretchable to 1.5×1.5 times at 90° C., and could be heat-sealed with a polystyrene sheet to obtain a composite.

EXAMPLE 2

A compound having a weight average molecular weight of 130,000 obtained in accordance with Example 1 was extruded through a single screw extruder at a T die temperature of 90° C. to obtain a board having a thickness of 3 mm. The board thus obtained was irradiated with γ-ray at 20 Mrad to have the whole board subjected to crosslinking reaction. The crosslinked whole board swelled in distilled water and exhibited a water absorptivity scale factor of 8 times. The board exhibited substantially the same result also in a physiological saline solution.

EXAMPLE 3

0.84 part by weight of hexamethylene diisocyanate and a small amount of dibutyltin dilaurate were blended with 100 parts by weight of a polyalkylene oxide compound (weight average molecular weight: 20,000) obtained by having bisphenol A block-addition-polymerized with 85% ethylene oxide and 15% propylene oxide, and the blend was subjected to urethane-forming reaction at 100° C. to obtain a polymer having a weight average molecular weight of 250,000. The polymer thus obtained was extruded through a single screw extruder at a T die temperature of 90° C. to obtain a cast sheet having a thickness of 100 μm. The sheet thus obtained was irradiated with γ-ray at 10 Mrad to be crosslinked, and the water absorptivity scale factor of the sheet exhibited 13 times in a physiological saline solution and distilled water.

As mentioned above, the present invention provides a water-absorptive material having a satisfactory water-absorptivity not only in ion-exchanged water (deionized water) but also in ionic aqueous solution. Due to the difference in crystallinity, the polymer of the present invention can be stably and satisfactorily subjected to thermoplastic molding, and has an excellent gel-stability as a water-absorptive body, as compared with a polymer derived from ethylene oxide only.

Thus, the molded product of the present invention can be maintained without being dispersed in a fibrous substrate, and can be easily fabricated. Also, according to the present invention, it is possible to control a water-absorptivity by appropriately mixing a crosslinked polymer and an uncrosslinked polymer.

What is claimed is:

1. A water-absorptive, water-insoluble material obtained by crosslinking with an ionizing radiation or ultraviolet rays a hydrophilic high molecular compound having a weight average molecular weight of at least 10,000 obtained by reaction of (i) a polyalkylene oxide compound having an organic compound containing two active hydrogen groups addition-polymerized with an alkylene oxide comprising ethylene oxide as the main component and (ii) a polycarboxylic acid, a polycarboxylic acid anhydride, a lower alkyl ester of polycarboxylic acid or a diisocyanate.

2. The water-absorptive, water-insoluble material according to claim 1, wherein the water-absorptive material is in a form of a film or a sheet.

3. A method for producing a water-absorptive, water-insoluble molded product, which comprises (a) molding a hydrophilic high molecular compound obtained by reaction of (i) a polyalkylene oxide compound having an organic compound containing two active hydrogen groups addition-polymerized with an alkylene oxide comprising ethylene oxide as the main component and (ii) a polycarboxylic acid, a polycarboxylic acid anhydride, a lower alkyl ester of polycarboxylic acid or a diisocyanate, and (b) crosslinking the molded product by irradiation with an ionizing radiation or ultraviolet rays.

4. The method according to claim 3, wherein the absorbed dose of the ionizing radiation is in the range of from 0.5 to 20 Mrad.

* * * * *